(12) United States Patent
Erickson

(10) Patent No.: US 7,395,118 B2
(45) Date of Patent: Jul. 1, 2008

(54) SYSTEM AND METHOD FOR IMPLANTABLE STIMULATION LEAD EMPLOYING OPTICAL FIBERS

(75) Inventor: John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 582 days.

(21) Appl. No.: 10/947,027

(22) Filed: Sep. 22, 2004

(65) Prior Publication Data

US 2005/0070987 A1 Mar. 31, 2005

Related U.S. Application Data

(60) Provisional application No. 60/505,905, filed on Sep. 25, 2003.

(51) Int. Cl.
*A61N 1/00* (2006.01)
(52) U.S. Cl. .................................................... 607/116
(58) Field of Classification Search ............... 607/116, 607/119, 122
See application file for complete search history.

(56) References Cited

U.S. PATENT DOCUMENTS 5,454,837 A * 10/1995 Lindegren et al. ............. 607/9

6,643,425 B1 * 11/2003 Bowers et al. ............... 385/18
2002/0133216 A1 9/2002 Connelly et al.
2003/0204220 A1 10/2003 Forsberg

OTHER PUBLICATIONS

Beth A. Schueler et al., "MRI Compatibility and Visibility Assessment of Implantable Medical Devices", Journal of Magnetic Resonance Imaging 1999, pp. 596-603.

* cited by examiner

*Primary Examiner*—George R Evanisko
*Assistant Examiner*—Amanda Patton
(74) *Attorney, Agent, or Firm*—Christopher S. L. Crawford; Peter Lando; Melissa Acosta

(57) ABSTRACT

An implantable lead, and method of manufacturing same, and a system and method for stimulation. The lead has proximal and distal ends having, respectively, a connector portion with a terminal and an electrode. An optically switched device is electrically connected to the electrode and to the terminal. An optical fiber is optically coupled to the connector portion at one end and to the optically switched device at another end. The optically switched device conducts a stimulus from the terminal to the electrode in response to an optical signal transmitted over the optical fiber.

3 Claims, 3 Drawing Sheets

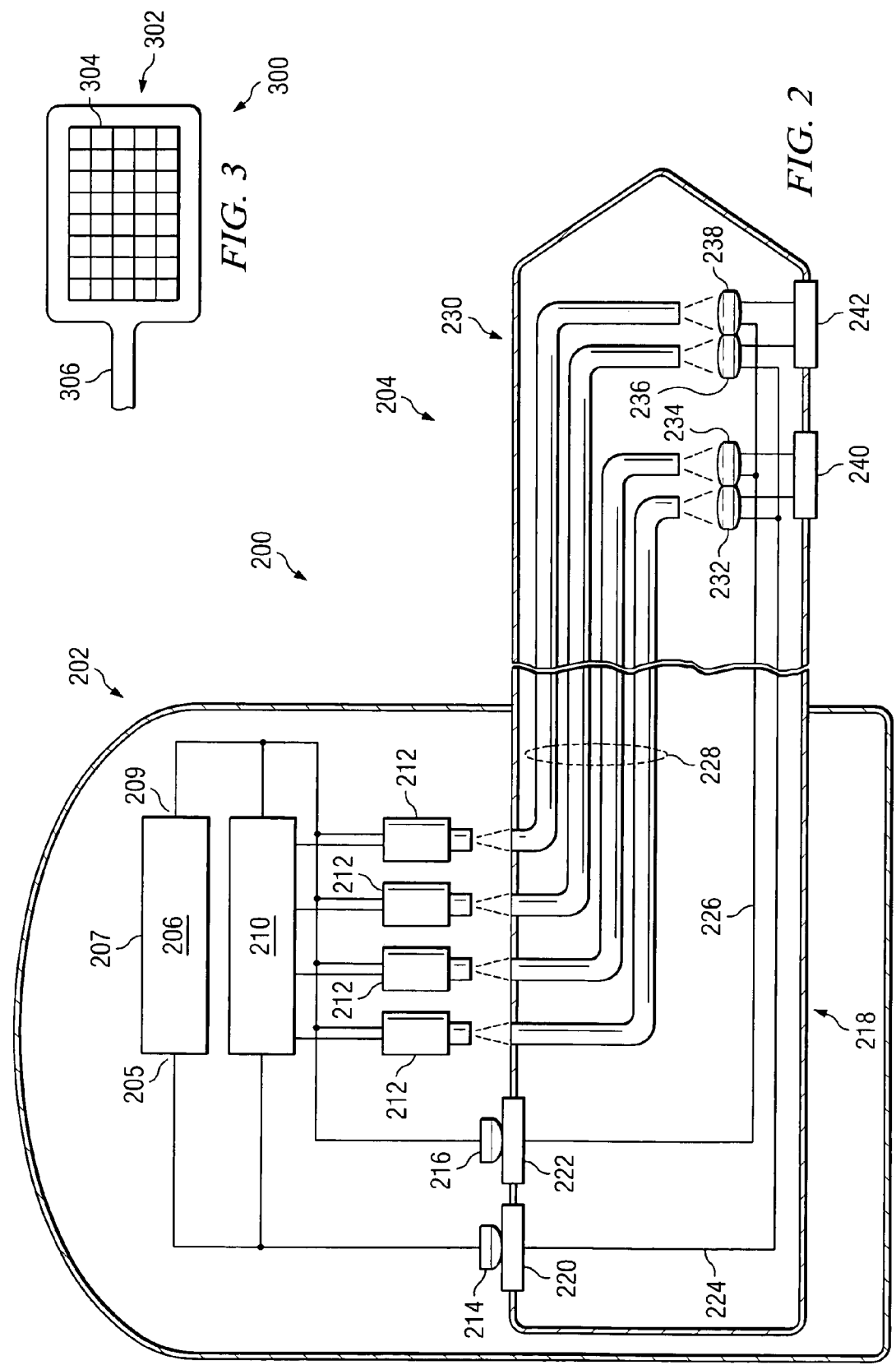

SYSTEM AND METHOD FOR IMPLANTABLE STIMULATION LEAD EMPLOYING OPTICAL FIBERS

CROSS-REFERENCE TO RELATED APPLICATIONS

This application claims benefit and priority (under 35 U.S.C. §119(e)) to prior U.S. provisional application Ser. No. 60/505,905 filed on Sep. 25, 2003, and which is incorporated herein by reference.

TECHNICAL FIELD OF THE INVENTION

The present invention relates to electrical leads, and in particular, an electrical lead for use in the medical field.

BACKGROUND

Implantable leads having electrodes are used in a variety of applications, including the delivery of electrical stimulation to surrounding tissue, neural or otherwise. Some leads include lumens (or channels) for the delivery of other elements, including chemicals and drugs. Whether in a stimulation or element delivery capacity, such leads are commonly implanted along nerves, within the epidural or intrathecal space of the spinal column, and around the heart, brain, or other organs or tissue of a patient.

Generally, several elements (conductors, electrodes and insulation) are combined to produce a lead body. A lead typically includes one or more conductors extending the length of the lead body from a distal end to a proximal end of the lead. The conductors electrically connect one or more electrodes at the distal end to one or more connectors at the proximal end of the lead. The electrodes are designed to form an electrical connection or stimulus point with tissue or organs. Lead connectors (sometimes referred to as terminals, contacts, or contact electrodes) are adapted to electrically and mechanically connect leads to implantable pulse generators or RF receivers (stimulation sources), or other medical devices. An insulating material typically forms the lead body and surrounds the conductors for electrical isolation between the conductors and for protection from the external contact and compatibility with a body.

Such leads are typically implanted into a body at an insertion site and extend from the implant site to the stimulation site (area of placement of the electrodes). The implant site is typically a subcutaneous pocket that receives and houses the pulse generator or receiver (providing a stimulation source). The implant site is usually positioned a distance away from the stimulation site, such as near the buttocks or other place in the torso area. In most cases, the implant site (and insertion site) is located in the lower back area, and the leads may extend through the epidural space (or other space) in the spine to the stimulation site (middle or upper back, or neck or brain areas).

Current lead designs have different shapes, such as those commonly known as percutaneous and paddle-shaped leads. Paddle leads, which are typically larger than percutaneous leads, are directional and often utilized due to desired stimulus effect on the tissues or areas. However, current paddle-shaped leads require insertion using surgical means, and hence, removal through surgical means.

Percutaneous leads are designed for easy introduction into the epidural space using a special needle. Therefore, such leads are typically smaller and more nearly circular in cross-section than paddle-shaped leads. This reduced size facilitates their implantation in the body, allows their implantation into more areas of the body, and minimizes the unwanted side effects of their implantation.

Larger cross-section leads are required, however, when greater numbers of electrodes are employed at the distal end of a lead. Several benefits can be gained from increasing the number of electrodes on a lead. More electrodes of smaller size allow a stimulation pattern to be more precisely localized, reducing unwanted stimulation of nearby areas and minimizing stimulation side effects. With more electrodes available, stimulation patterns can be moved from the electrodes selected during and immediately after implantation to other electrodes on the lead in order to adapt to post-implantation migration of the lead and changes in the body's responsiveness to stimulation. The presence of more electrodes permits adjacent electrodes to be employed in anode-cathode combinations for increased control of the directionality and penetration of stimulation patterns. However, an increase in the number of electrodes results in an increased number of conductors in the lead body and, thus, in leads of larger cross-section.

Smaller diameter conductors may be employed, in order to reduce the lead body diameter, but such conductors have a higher resistivity than larger diameter conductors. As will be understood by one skilled in the art, a higher resistivity conductor produces a greater voltage drop through the conductor, and thus delivers a lower stimulation voltage at the distal end electrode than would be delivered by a lower resistivity conductor. Greater resistivity in the conductor also results in less current being delivered at the stimulation site. More power is lost in the conduction of the stimulation signal through a higher resistivity conductor, and in some cases, requires more frequent recharging of the power source in the implantable medical device.

Rather than adding conductors to the lead body, an embedded controller may be employed at the distal end of the lead to control a greater number of electrodes with fewer conductors. Known techniques of signal multiplexing may be used to implement the embedded controller. Alternatively, microcontrollers may be used, and the desired stimulation pattern communicated from the connector at the proximal end of the lead to the microcontroller at the distal end using digital communication techniques. While such solutions permit a reduced cross-section in the lead body, they require an increased cross-section at the distal end of the lead to accommodate the circuitry required to implement the solution.

The presence of metallic conductors in stimulation leads can cause side effects when magnetic resonance imaging (MRI) is employed, as well. Currents and voltages induced in the conductors by the electromagnetic field of a MRI scanner may result in uncontrolled stimulation of nerves near the electrodes of a stimulation lead or, in extreme cases, in nerve damage. Such results have led the FDA and manufacturers of implantable medical devices to issue a contraindication for the use of MRI with patients with such devices implanted.

Many other problems and disadvantages of the prior art will become apparent to one skilled in the art after comparing such prior art with the present invention as described herein.

SUMMARY

The present invention provides an implantable stimulation lead of reduced cross-section with a reduced number of metallic conductors.

According to one embodiment of the present invention, there is provided a lead with proximal and distal ends having, respectively, a connector portion with a terminal and an electrode. An optically switched device is electrically connected to the electrode and to the terminal. An optical fiber is optically coupled to the connector portion at one end and to the optically switched device at another end.

In another embodiment of the present invention, there is provided a lead with proximal and distal ends having, respectively, a connector portion and an electrode. An optically switched device is electrically connected to the electrode. An optical fiber, optically coupled to the connector portion, illuminates an adjustable mirror device, and light reflected from the mirror device illuminates the optically switched device.

In yet another embodiment of the present invention, there is provided a method of administering a stimulus with a stimulation device. The method includes activating a light source in an illumination pattern that corresponds to a desired stimulation pattern. Light from the light source is conducted by an optical fiber to an optically switched device, which administers the stimulus in response to the light pattern.

In still another embodiment of the present invention, there is provided a method of administering a stimulus with a stimulation device. The method includes optically coupling a light source to one end of an optical fiber and an optically switched device to another end of the optical fiber. One terminal of the optically switched device is electrically connected to a power source and another terminal is electrically connected to a stimulation electrode. The stimulus is administered at the stimulation electrode in response to light emitted by the light source.

In another embodiment of the present invention, there is provided a method of manufacturing a lead. An implantable lead is provided with proximal and distal ends having, respectively, a connector portion with a terminal and an electrode. The method includes electrically connecting a first conductor to the first terminal and the optically switched device, and optically coupling a first optical fiber at a first end to the connector portion and at a second end to the optically switched device.

In another embodiment of the present invention, there is provided a system for stimulating a portion of the body. The system includes a stimulus source and an implantable lead. The lead has proximal and distal ends with, respectively, a connector portion with a terminal and an electrode. An optically switched device is electrically connected to the electrode and to the terminal. An optical fiber is optically coupled to the connector portion at one end and to the optically switched device at another end.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which:

FIG. 2 presents a schematic of another system embodying the invention;

FIG. 3 shows a multi-electrode stimulation paddle; and

DETAILED DESCRIPTION OF THE INVENTION

An optical fiber is a thin strand of glass or plastic that conducts light by the principle of internal reflection. Light entering one end of the fiber exits the other end. If the light illuminating one end of the fiber is modulated, that modulation is preserved during transmission and is present in the light emitted from the other end of the fiber. An optical fiber is typically smaller than the typical metallic electrical conductor. Such conductors are typically around 0.25 millimeters in diameter, while an optical fiber is typically between about 250 micrometers and 125 micrometers and may be smaller.

Figure 1:
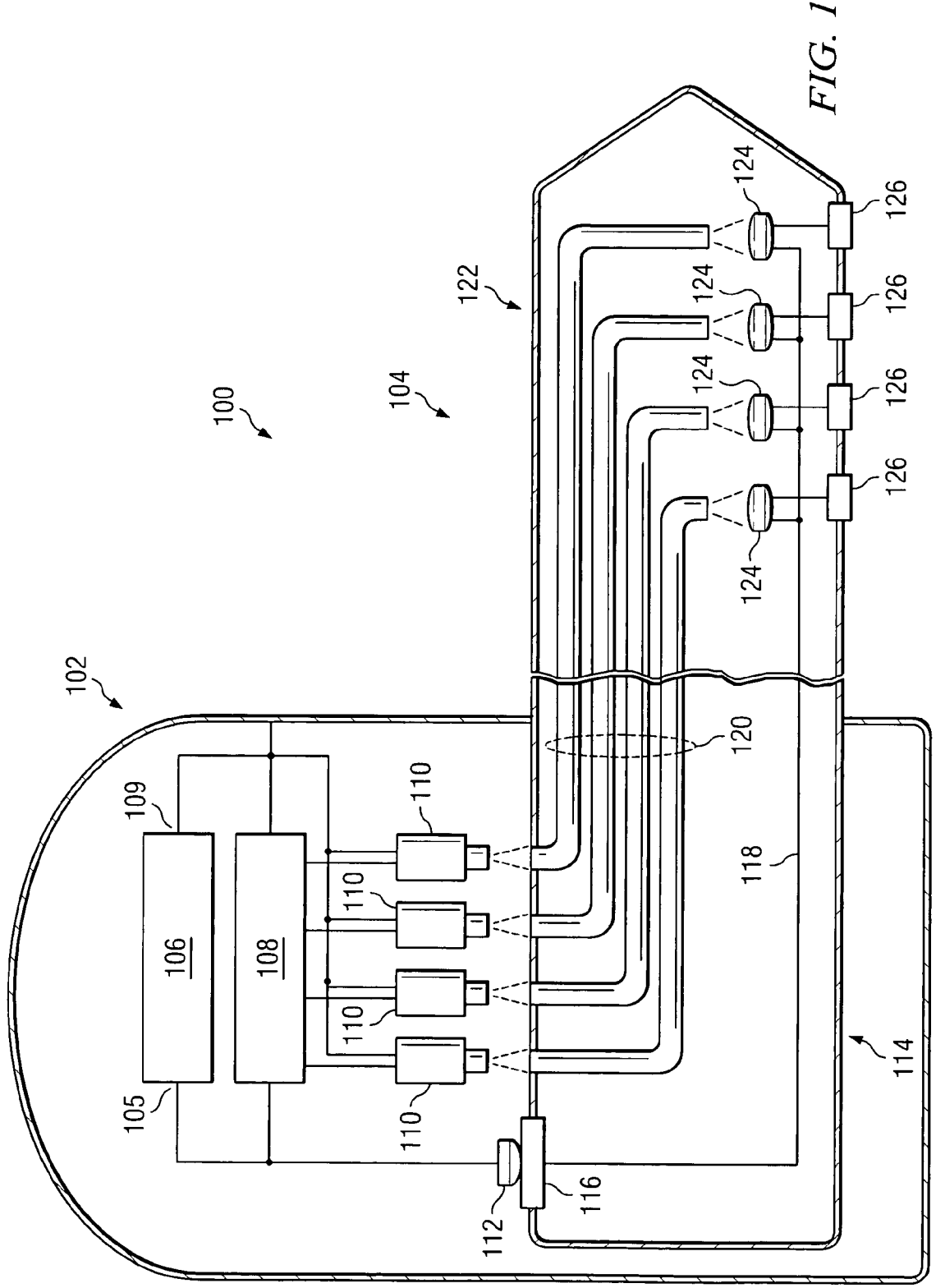
FIG. 1 is a schematic view of a preferred embodiment of an implantable electrical stimulation system according to the present invention.

FIG. 1 shows a schematic view of one embodiment of the present invention, in which optical fibers are employed in an implantable lead to carry stimulation signals from an implantable medical device to the stimulation site. An implantable stimulation system 100 comprises a medical device 102 (in this embodiment an implantable pulse generator (IPG)) and a lead 104. After surgical or percutaneous insertion of the lead 104 into the body, the lead 104 is connected to the medical device 102, typically, by inserting a connector portion 114 of the lead 104 into the medical device 102, wherein the connector portion 114 is secured by springs, set screws or other mechanism (not shown).

The medical device 102 includes a power source 106 and a stimulation control circuit 108. The power source 106 is electrically connected to the stimulation control circuit 108. Additionally, a terminal 109 of the power source 106 is electrically connected to the conductive case of the medical device 102. A terminal 105 of the power source 106 is electrically connected to a contact 112. The stimulation control circuit 108 stores one or more desired stimulation patterns and reproduces those patterns on light sources 110 (in this embodiment, light emitting diodes). When the administration of a stimulation voltage is desired, the stimulation control circuit 108 activates one or more light sources 110. When the desired period of stimulation is ended, the circuit 108 deactivates the one or more light sources 110. In the alternative, stimulation voltage may be administered when the light source(s) are deactivated and ended when the light source is activated.

Each of the light sources 110 individually illuminates a proximal end of a corresponding one of optical fibers 120 that extend substantially the length of the lead 104. These proximal ends are mounted in the connector portion 114 of the lead 104. Also mounted in the connector portion 114 of the lead 104 is a terminal 116, which makes electrical contact with the contact 112.

The distal portion 122 of the lead 104 includes one or more optically switched devices 124. The optically switched devices 124 may be photodiodes, phototransistors, photodarlingtons or any other photosensitive device or photosensitive circuit whose electrical conductivity is controlled by the amount of received light. The distal ends of individual ones of optical fibers 120 illuminate each of optically switched devices 124. A conductor 118 is electrically connected to each optically switched device 124 and provides electrical power from the terminal 116 to the optically switched devices 124. The output of each optically switched device 124 is electrically connected to one of electrodes 126 at the distal end 122 of the lead 104. The electrodes 126 produce electrical stimulation of the nerves, muscles, or other tissues at the stimulation site when the lead 104 is implanted within a body. In the embodiment shown in FIG. 1, the human body itself completes the electrical circuit back to the conductive case of the medical device 102.

In operation, the stimulation control circuit 108 activates the light sources 110 in a desired stimulation pattern. The output (light) from the activated light sources 110 is input to the proximal ends of the associated ones of optical fibers 120 and is conducted (or transmitted) along the fibers to the distal ends, where the light signal illuminates the associated ones of optically switched devices 124. The optically switched devices 124 coupled to the active light sources 110 are activated and conduct, thereby applying a voltage to the associated ones of electrodes 126. As a result, the desired stimulation pattern is produced at the stimulation site.

In an alternative embodiment of the invention (not shown), the power source 106 is located outside the housing of the medical device 102 and electrically connected to the device by a cable. In another embodiment (not shown), such an externally located power source may deliver power to the medical device 102 through a wireless connection, such as RF or inductive conduction.

In another embodiment of the invention (not shown), the stimulation system 100 is fabricated as an integral unit, with the lead 104 forming a 'pigtail', permanently attached to the medical device 102. In such an embodiment, the connector portion 114 would not be required, as the external body of the lead 104 would be permanently sealed to the housing of the medical device 102, the conductor 118 permanently connected to the power supply 106 without the need for the terminal 116 and the contact 112, and the proximal ends of the optical fibers 120 mechanically mounted within the housing of the medical device 102 so as to be optically coupled with the light sources 110.

In yet another embodiment of the invention (not shown), a switch, controlled by the stimulation control circuit 108, would be employed to connect the contact 112 in alternation to the terminals 105 and 109 of the power source 106. The terminal 105 carries a first voltage and the terminal 109 carries a second voltage, each with reference to the other terminal. By illuminating the light sources 110 at appropriate, times, the stimulation control circuit 108 causes the optical switches 124 to switch either the first or second voltage onto the distal electrodes 126, thereby causing them to operate in a tri-state stimulation mode.

Turning to FIG. 2, another embodiment of the present invention is presented in schematic form. An implantable stimulation system 200 includes a medical device 202 and a lead 204. The lead 204 is connected to the medical device 202, in this embodiment, by inserting a connector portion 218 of the lead 204 into the medical device 202.

The medical device 202 includes a power source 206, outputting two supply voltages. A power source terminal 205 provides a first voltage and a power source terminal 209 provides a second voltage. The power supply terminals 205 and 209 are electrically connected to contacts 214 and 216, respectively. As described for the embodiment in FIG. 1, the power source 206 could alternatively be located outside the housing of the medical device 202 and electrically connected to the device with a cable or through wireless means.

A stimulation control circuit 210 is electrically connected to the power source terminals 205 and 209. The stimulation control circuit 210 activates light sources 212 in a desired stimulation pattern, and the light sources 212 individually illuminate the proximal ends of optical fibers 228.

The optical fibers 228 extend substantially the length of the lead 204, and the proximal ends of optical fibers 228 are mounted in connector portion 218 of the lead. The connector portion 218 includes lead terminals 220 and 222, which make electrical contact with the contacts 214 and 216, respectively, when the lead 204 is connected to the medical device 202. A distal end 230 of the lead 204 includes optically switched devices 232, 234, 236 and 238. A distal end of each of the optical fibers 228 illuminates each of optically switched devices 232, 234, 236 and 238.

A conductor 224 electrically connects a first terminal of each of the optically switched devices 232 and 236 to the lead terminal 220. Similarly, a conductor 226 electrically connects a first terminal of each of the optically switched devices 234 and 238 to the lead terminal 222. A stimulation electrode 240 in the distal end 230 of the lead 204 is electrically connected to a second terminal of the optically switched devices 232 and 234. A stimulation electrode 242 is electrically connected to a second terminal of the optically switched devices 236 and 238.

Individual ones of light sources 212 are optically coupled to individual ones of optical fibers 228. Individual ones of optical fibers 228 are, in turn, coupled to individual ones of optically switched devices 232, 234, 236 and 238. The light sources activated by the stimulation control circuit 210 illuminate their associated optical fibers, which in turn illuminate their associated optically switched devices. When the optically switched devices 232 and 236 are illuminated, they conduct the first voltage from the conductor 224 to the associated stimulation electrodes 240 and 242, respectively. Similarly, illumination of the optically switched devices 234 and 238 applies the second voltage from the conductor 226 to the electrodes 240 and 242, respectively. Thus, the stimulation electrodes 240 and 242 operate in a tri-state stimulation mode: depending on the illumination of the associated optically switched devices, the stimulation electrodes 240 and 242 provide either a first or second stimulation voltage, or no voltage at all, to the surrounding tissue.

In an alternative embodiment of the invention (not shown), a light source producing light of selectable wavelengths (colors, frequencies) or a plurality of light sources, each emitting different wavelengths, are employed. A single optical fiber optically couples the light source(s) to a plurality of optical switches sensitive to different wavelengths of light, thereby controlling a plurality of optical switches with a single optical fiber.

The power conducted by the optical switches 232, 234, 236 and 238 may be generated at the distal end 230 of the lead 204 in another embodiment of the invention (not shown). In this embodiment, the contacts 214 and 216 are replaced by a single light source, electrically connected to both the terminals, 205 and 209, of the power source 206, such that it is continuously illuminated. The conductors 224 and 226 are replaced with a single optical fiber, with a proximal end of the single optical fiber mounted in the connector portion 218 and optically coupled to the single light source. A distal end of the single optical fiber illuminates a photovoltaic device. Output terminals of the photovoltaic device are electrically connected to the optical switches 232 and 236, and 234 and 238. In this embodiment, the body of the lead 204 contains only optical fibers, and the elimination of all wire conductors further reduces the size of the lead 204.

In yet another embodiment of the invention (not shown), the contacts 214 and 216, the terminals 220 and 222, and the conductors 224 and 226 are eliminated. Photovoltaic devices replace the optical switches 232, 234, 236 and 238 and are optically coupled to the optical fibers 228. The electrodes in the distal end 230 of the lead 204 are electrically connected to the output terminals of the photovoltaic devices, such that a voltage produced when the photovoltaic devices are illuminated supplies the stimulus administered to the surrounding tissue. In this embodiment, too, the body of the lead 204 contains only optical fibers, which may reduce its size.

While the above descriptions are of neurostimulation systems, it will be appreciated by one skilled in the art that the techniques of the present invention may also be embodied in other stimulation systems—including pacemakers, cochlear implants, or deep-brain stimulation systems. It will be further understood that, while FIGS. 1 and 2 show stimulation leads having four and two electrodes, respectively, any number of electrodes may be employed, as desired, without departing from the spirit and scope of the invention.

Furthermore, while FIGS. 1 and 2 show a one-to-one relationship between light sources and optical fibers, and between optical fibers and optically switched devices, other embodiments of the invention may utilize a one-to-plural or plural-to-one relationship in either situation. It will be understood that a single medical device may provide stimulation power and stimulation control signals for a plurality of stimulation leads. It will also be appreciated by one skilled in the art that a photosensitive device may apply a stimulation voltage to an electrode in response to the absence of illumination, rather than in response to its presence.

FIG. 3 shows a planar, multi-electrode stimulation paddle such as may be used in a stimulation system. In this embodiment of the invention, the paddle forms a distal end 302 of a lead 300. A lead body 306 connects the paddle to a proximal end of the lead (not shown) having a connector portion including terminals (also not shown) similar to the connector portions of the leads of FIGS. 1 and 2. Stimulation electrodes 304 are, in this embodiment, a rectangular array of electrically isolated electrodes, which can be individually energized to produce a desired stimulation pattern at a desired location on the array.

Figure 4:
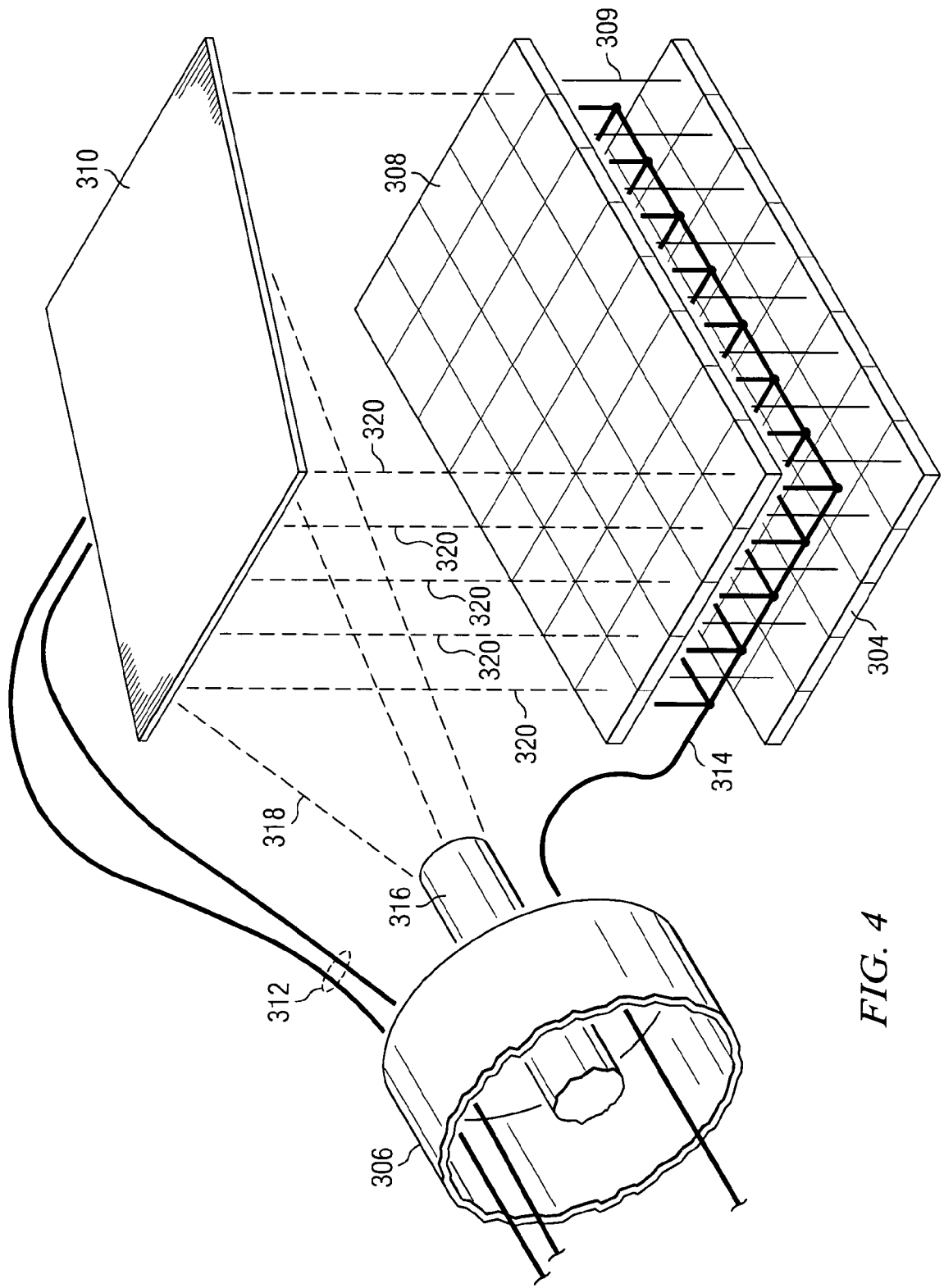
FIG. 4 is a schematic view of an embodiment of the present invention for controlling the paddle of FIG. 3.

FIG. 4 presents a schematic view of the interior of the stimulation paddle of FIG. 3. In this view, the lead body 306 and the electrode array 304 can be seen, but the paddle body of the distal end 302 of the lead 300 has been eliminated to show the interior of the paddle. Conductors 309 electrically connect an array 308 of optically switched devices to the electrode array 304. In this embodiment of the invention, individual photosensitive devices are connected to individual electrodes. The optically switched devices 308 are also electrically connected to a distal end of a conductor 314, which conducts a stimulation voltage from a terminal in the connector portion (not shown) of the lead 300. If tri-state operation is desired, as in the embodiment of FIG. 2, two such conductors 314 may be provided, carrying positive and negative stimulation (relative to each other), respectively, and pairs of photosensitive devices may be electrically connected to each electrode in the array 304.

An optical fiber 316 in the lead body 306 illuminates the entirety of a digital micromirror device (DMD) 310, such as the 0.55SVGA DDR device, manufactured by Texas Instruments, as indicated by reference numeral 318. A lens or lens system may be employed to produce the divergence pattern needed to illuminate the DMD 310. The DMD 310 is shown with a rectangular array of hinge-mounted microscopic mirrors and control circuitry. The mirrors can be tilted to one of two positions: in one position, the mirrors reflect the illumination 318 from the optical fiber 316 away from the optically switched devices 308; in the other position, the mirrors reflect the illumination 318 onto the optically switched devices 308, as indicated by reference numeral 320. Each photosensitive device in the array 308 is illuminated by light reflected from one or more mirrors in the DMD 310. The control circuitry of the DMD 310 is electrically connected to distal ends of conductors 312, which are electrically connected at their proximal ends to terminals (not shown) in a connector portion of the lead 300. As will be appreciated, the control circuitry of the DMD 310 is shown at or near the lead 300, however the circuitry may be located at the device 202.

In operation, control signals on the conductors 312 cause selected ones of the mirrors of the DMD 310 to tilt into position to illuminate selected ones of the optically switched devices 308, thereby causing the electrodes in array 304 that are associated with the illuminated devices to apply stimulation energy in a desired pattern to the surrounding tissue.

While FIG. 4 illustrates an embodiment in which a digital micromirror device is used both to split the light from the optical fiber 316 into multiple beams and to direct those beams onto and away from the optical switches 308, other techniques may be used to perform these two functions. For example, a diffraction grating may be used to split the light from the optical fiber 316 into multiple beams. Similarly, a bank of microelectromechanical system (MEMS) actuators may individually pass or block those beams in order to selectively illuminate optical switches or photovoltaic devices.

It will be appreciated that the conductors 312 may be wire conductors or may be optical fibers coupled by suitable conversion circuitry to the electrical control inputs of the DMD 310. One skilled in the art will also appreciate that optical fibers may be employed in place of wire conductors to communicate with prior art embedded controllers in multi-electrode stimulation leads.

While the figures show leads containing only electrical conductors and optical fibers, it will be appreciated that implantable stimulation leads embodying the present invention may also incorporate one or more lumens for the delivery of drugs or other chemicals. A lead according to the invention may also include a stylet passage for receiving a stylet to provide better control over the lead during placement.

Aspects of the present invention can be used for any implantable devices, such as light actuated MEMS control devices, and control valves for drug delivery in implantable devices.

It may be advantageous to set forth definitions of certain words and phrases that may be used within this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, such a device may be implemented in hardware, firmware or software, or some combination of at least two of the same. It should be noted that the functionality associated with any particular controller may be centralized or distributed, whether locally or remotely.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

What is claimed is:

1. A lead for applying stimulation pulses to tissue of a patient, comprising:
a lead body;
first and second terminals disposed on a proximal end of the lead body;
a plurality of electrodes disposed on a distal end of the lead body;

first and second electrical conductors disposed within the lead body, the first and second electrical conductors extending substantially from the proximal end to the distal end of the lead body, the first and second electrical conductors being electrically coupled to the first and second terminals respectively;

a plurality of optical fibers; and first and second pluralities of photo-sensitive circuits, wherein each photo-sensitive circuit has a conductivity controlled by an amount of light incident on the respective photo-sensitive circuit;

wherein the first plurality of photo-sensitive circuits are coupled in parallel with each other to the first conductor with each photo-sensitive circuit of the first plurality of photo-sensitive circuits electrically coupling a respective electrode of the plurality of electrodes to the first conductor;

wherein the second plurality of photo-sensitive circuits are coupled in parallel with each other to the second conductor with each photo-sensitive circuit of the second plurality of photo-sensitive circuits electrically coupling a respective electrode of the plurality of electrodes to the second conductor;

wherein each optical fiber is optically coupled to a respective photo-sensitive circuit of the first and second pluralities of photo-sensitive circuits to control current flow originating from one of the first and second terminals and flowing between a corresponding electrode and one of the first and second conductors through the respective photo-sensitive circuit subject to illumination by the optical fiber.

2. The lead in accordance with claim 1 wherein each photo-sensitive circuit is a one of a photodiode and a phototransistor.

3. A system for electrically stimulating tissue of a patient, comprising:

a lead for applying stimulation pulses to tissue of a patient, comprising:

a lead body;

first and second terminals disposed on a proximal end of the lead body;

a plurality of electrodes disposed on a distal end of the lead body;

first and second electrical conductors disposed within the lead body, the first and second electrical conductors extending substantially from the proximal end to the distal end of the lead body, the first and second electrical conductors being electrically coupled to the first and second terminals respectively;

a plurality of optical fibers; and first and second pluralities of photo-sensitive circuits, wherein each photo-sensitive circuit has a conductivity controlled by an amount of light incident on the respective photo-sensitive circuit;

wherein the first plurality of photo-sensitive circuits are coupled in parallel with each other to the first conductor with each photo-sensitive circuit of the first plurality of photo-sensitive circuits electrically coupling a respective electrode of the plurality of electrodes to the first conductor;

wherein the second plurality of photo-sensitive circuits are coupled in parallel with each other to the second conductor with each photo-sensitive circuit of the second plurality of photo-sensitive circuits electrically coupling a respective electrode of the plurality of electrodes to the second conductor;

wherein each optical fiber is optically coupled to a respective photo-sensitive circuit of the first and second pluralities of photo-sensitive circuits to control current flow originating from one of the first and second terminals and flowing between a corresponding electrode and one of the first and second conductors through the respective photo-sensitive circuit subject to illumination by the optical fiber;

an implantable pulse generator comprising:

pulse generating circuitry for generating electrical pulses for delivery to the first and second terminals, the pulse generating circuitry coupling an anode output and a cathode output to the first and second terminals respectively during delivery of an electrical pulse; and one or more optical sources for generating optical power for transmission through the plurality of optical fibers of the lead;

stimulation control circuitry for controlling delivery of electrical pulses through one or more electrodes of the lead, the stimulation control circuitry selecting a unique set of optical fibers of the plurality of optical fibers to receive optical power from the one or more optical sources in relation to electrode polarities selected for a respective stimulation pulse.

* * * * *

UNITED STATES PATENT AND TRADEMARK OFFICE
CERTIFICATE OF CORRECTION

| | |
|---|---|
| PATENT NO. | : 7,395,118 B2 |
| APPLICATION NO. | : 10/947027 |
| DATED | : July 1, 2008 |
| INVENTOR(S) | : John H. Erickson |

Page 1 of 1

It is certified that error appears in the above-identified patent and that said Letters Patent is hereby corrected as shown below:

Column 10, line 34, delete "and"; line 37, add --and-- after "of the lead;".

Signed and Sealed this

Nineteenth Day of August, 2008

JON W. DUDAS
*Director of the United States Patent and Trademark Office*